United States Patent
Yadav et al.

(10) Patent No.: US 8,685,423 B2
(45) Date of Patent: Apr. 1, 2014

(54) CONTROLLING MEALYBUGS

(75) Inventors: Mayank Yadav, New Delhi (IN);
Suresh Ramachandran, Thane (IN);
Sanjoy Kundu, Navi Mumbai (IN)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/359,540

(22) Filed: Jan. 27, 2012

(65) Prior Publication Data

US 2012/0195974 A1 Aug. 2, 2012

Related U.S. Application Data

(60) Provisional application No. 61/437,027, filed on Jan. 28, 2011.

(51) Int. Cl.
*A01N 25/32* (2006.01)
*A01N 43/40* (2006.01)
*A01N 57/14* (2006.01)

(52) U.S. Cl.
USPC ............. 424/406; 424/405; 424/409; 514/89; 514/357

(58) Field of Classification Search
USPC .................................... 514/89, 357
See application file for complete search history.

(56) References Cited

U.S. PATENT DOCUMENTS

2008/0287506 A1 11/2008 Roush et al.
2011/0207606 A1 * 8/2011 Satchivi et al. ............... 504/105

FOREIGN PATENT DOCUMENTS

| WO | WO-2009/134224 | * 10/2009 |
| WO | WO 2010/126580 A1 | 11/2010 |
| WO | PCT/US2012/022815 | 1/2012 |

OTHER PUBLICATIONS

"Pesticide Mixtures" by Dr. Raymond A. Cloyd, Chapter Six, p. 71 in Pesticides—Formulations, Effects, Fate, Prof. Margarita Stoytcheva (Ed.).
"The Unique Role of Halogen Substituents in the Design of Modern Agrochemicals" Dr. Peter Jeschke, Pest Manag Sci 2010; 66: 10-27, 24.
"Synergism—A Patent View" by David L. Richer, in Pestic. Sci. 1987. 19, 309-315.
"IRAC MoA Classification Scheme" Insecticide Resistance Action Committee, Issued Apr. 2012, Version 7.2.

* cited by examiner

*Primary Examiner* — Neil Levy
(74) *Attorney, Agent, or Firm* — Carl D. Corvin

(57) ABSTRACT

The invention disclosed in this document concerns controlling mealybugs.

1 Claim, No Drawings

CONTROLLING MEALYBUGS

CROSS-REFERENCE TO RELATED APPLICATIONS

This application claims priority from U.S. provisional application 61/437,027 filed on Jan. 28, 2011. The entire content of this provisional application is hereby incorporated by reference into this application.

FIELD OF THE INVENTION

The invention disclosed in this document is related to the field of controlling mealybugs.

BACKGROUND OF THE INVENTION

Cotton has been grown for about 7,000 years. In 2009 about 45 billion pounds of cotton was produced. Mealybugs are a recent pest to harming cotton crops around the world. In June of 2008, The International Cotton Advisory Committee reported that the mealybug was a new threat to cotton and that pyrethroid insecticides are not effective against mealybugs. Furthermore, it was reported that an effective insecticide has yet to be found ("Mealy Bug: A New Threat to Cotton Production in Pakistan and India" The ICAC Recorder, VOL. XXVI No. 2, pages 15-19 Jun. 2008). A solution to this new threat is needed.

DETAILED DESCRIPTION OF THE INVENTION

During the last few years mealybugs, which were considered to be minor pests in many crops, have acquired the status of major pests, especially in cotton, vegetables, and fruits. Recently in India the cotton crop in Punjab, Rajasthan, Maharashtra, and Gujarat, was seriously infested with mealybugs. During 2005, the sudden appearance of this pest on cotton in Multan, Sanghar, Mirpurkhas, and Tando Allahyar of Pakistan destroyed an entire crop within a few days.

Mealybugs (Homoptera: Pseudococcidae) are cottony in appearance, small oval, soft-bodied, sucking insects. Adult mealybugs are found on leaves, stems, and roots of plants. The insects themselves are covered with white mealy wax, which reduces the effectiveness of many insecticides, thereby making them more difficult to eradicate. Mealybugs form colonies on stems and leaves developing into dense, waxy, white masses. These insects can suck a large amount of sap from leaves and stems with the help of their piercing/sucking mouth parts, depriving plants of essential nutrients. Excess sap, which is produced as a result of a mealybug infestation, is excreted as honeydew which attracts ants. These ants then protect the mealy bugs from other predators that would help control the mealy bugs. Many plants infested with mealybugs develop a sooty mold which inhibits the infected plant's ability to manufacture food and may ultimately kill the plant.

Mealybugs range from white to pink in color and measure about 3-4 mm in length. In case of M. hirsutus, both eggs and crawlers are pink in color. The crawlers measure 0.3 mm in length. Immature females and newly matured females are grayish-pink which are dusted with mealy white wax. Adult females are about 2.5 mm long, soft-bodied, elongate oval and slightly flattened. Females are provided with 9-segmented antennae, anal lobe bars, numerous dorsal oral rim ducts on all parts of the body except the limbs and long, flagellate dorsal setae. Males have one pair of very simple wings, long antennae and white wax filaments projecting posteriorly with no mouthparts.

Reproduction in most species is by parthenogenesis, but some species such as M. hirsutus are bi-parental. The mature female lays eggs in an egg sac of white wax, usually in clusters on the twigs, branches, or bark of the host plant but sometimes on the plant's leaves and terminal ends. Each egg sac may contain as many as 600 eggs, majority of which are female resulting in explosive outbreak. Some species such as D. brevipes are ovoviviparous i.e. the eggs hatch within the female and give births live larvae.

The eggs are minute, varying from 0.3 to 0.4 mm in length. Egg development takes between 3 and 9 days. Eggs hatch into nymphs called crawlers which are very mobile. In appearance, nymphs of both sexes resemble female adults. There are three nymphal instars in female and four in males which lasts for 22-25 days. The last instar of the male is an inactive stage in which the animals possess wing buds within a cocoon of mealy wax. Under normal conditions individual mealybugs may take as long as 30 days to grow through all the nymphal stages.

Most species survives cold conditions as eggs or other stages, both on the host plant and in the soil. In warm climates, the insects stay active and reproduce year-round. Under conditions conducive to growth there may be as many as 15 generations per year.

Non-infected plants can be infected from infected plants as juvenile mealybugs can crawl from an infected plant to another plant. In addition, small 'crawlers' are readily transported by wind, rain, birds, ants, clothing and vehicles, and may settle in cracks and crevices, usually on new plants. The wax, which sticks to each egg, also facilitates passive transport by equipment, animals, or people. In fact, humans and human activity may inadvertently aid in the transport of mealybugs and contribute to new infestations. The most likely mechanism for long-distance movement of these insects is probably through the human transport of infested planting material and fresh fruit and vegetables across the country or even from one end of a farm to the other. Ants, attracted by the honeydew, have been seen carrying mealybugs from plant to plant. Once established on a give plant, colonies of mealybugs may readily migrate from shoot tips to twigs, branches and finally down the trunk of the plant.

Damage to infected plants is readily apparent as infested growing points on plants become stunted and swollen; the degree of these symptoms may vary depending upon the susceptibility of each host species. Heavy clustering of mealybugs may be apparent under leaf surface giving the appearance of a thick mat with waxy secretion. And severe infestations resemble patches of cotton all over the plant.

Both nymphs and adults of the insect suck the sap from leaves causing withering and yellowing of leaves. Fruit may drop prematurely on crop plants. Heavy infestation can cause defoliation and even death of the plant. Mealybug infestations also affect the development of flowers and stems (especially in succulents with fleshy stems). When fruits are infested, they can be entirely covered with the white, waxy coating of the mealybug. Infestation can lead to fruit drop, or fruit may remain on the host in a dried and shriveled condition. In general, mealybug infected fruits are unmarketable.

In cotton serious attack results in retarded growth and late opening of bolls, affecting the yield badly. The insects feed on soft tissues and inject saliva that causes curling and contortion of leaves. The insects and the damage that they do may also contribute to the spread of other plant pathogens, for example, Citrus mealybug (P. citri), commonly found associated with black pepper (Piper nigrum) plants in India is known to transmit Badnavirus associated with stunted disease. Feeding of the species Dysmicoccus on pineapple produces a toxic effect called mealybug stripe, expressed as green or black striped areas. The most predominant symptom is wilting of leaves, commencing from leaf tips. A reddish-yellow color develops in infected plants in the wilting areas of the plants and in the final stages of an infestation the plants may rot and decay.

The sugary secretions (honeydew) of Mealybugs is known to attract ants, the ants in turn help spread the mealybugs and protect the mealybugs from predators of mealybugs such as ladybird beetles, parasites and other natural enemies. Ants also keep mealybug colonies clean from detritus that accumulate in the secreted honeydew, which may itself be harmful to the colony. In an even more overt symbiotic relationship, species of ants such as *Oecophylla smaragdina*, *Crematogaster* sp. and *Anoplolepis gracilipes* have been observed attending mealybug, *P. citri* while feeding on honeydew on *Hibiscus*.

The economic impact of mealybugs is widespread. In its native range, *M. hirsutus* has been recorded causing economic damage to many crops. In India alone, losses have been reported for cotton; the fiber crops *Hibiscus sabdariffa*, *Hibiscus cannabinus* and *Boehmeria nivea*; grapevine; mulberry; pigeonpea; *Zizyphus mauritiana*. Presumably, many ornamental woody plants are also affected, but populations and damage may be limited by natural enemies. In India, it is a major pest of grapes, reducing yields in some instances by 50 to 100 percent. Yield losses on other crops, such as jute and mesta may range up to 75 percent.

Some mealybugs of current commercial concern include the following species:
1. Striped mealybug (*Ferrisia virgata*);
2. Longtail mealybug (*Pseudococcus longispinus*);
3. Citrus mealybug (*Planococcus citri*);
4. *Solanum* mealybug (*Phenacoccus solani*);
5. Pink sugarcane mealybug (*Saccharicoccus sacchari*);
6. Pineapple mealybug (*Dysmicoccus brevipes*);
7. Pink mealybug (*Maconellicoccus hirsutus*, synonyms—*Phenacoccus hirsutus*):
8. Cotton mealybug (*Phenacoccus solenopsis*); and
9. Mango Mealybug (*Drosicha mangiferae*).

It has now been discovered that a synergistic mixture of Sulfoxaflor and Chlorpyrifos can applied to an area where mealybugs are located (such as where cotton is being grown) can control such mealybugs. Sulfoxaflor is a new pesticide and methods to produce it are know in the art, for example, see WO 2007/095229. Chlorpyrifos is a well know, readily available, pesticide and methods to produce it are known in the art, for example, see U.S. Pat. No. 3,244,586.

The mixture of Sulfoxaflor and Chlorpyrifos is generally used in the following amounts.

Synergistic Mixture Application Table

| Molecule | Amount to use in grams per hectare | | |
| --- | --- | --- | --- |
| | Broad | Broader | Broadest |
| Sulfoxaflor | 1-100 | 0.1-1000 | 0.01-5000 |
| Chlorpyrifos | 1-1000 | 0.1-2500 | 0.01-5000 |

Generally, the weight ratio of Chlorpyrifos to Sulfoxaflor is from about 100:1 to about 1:100, preferably from about 50:1 to about 1:50, and more preferably from about 10:1 to about 5:1. As a substitute for Chlorpyrifos, Chlorpyrifos-methyl may be used. Chlorpyrifos-methyl is a well know, readily available, pesticide and methods to produce it are known in the art, for example, see U.S. Pat. No. 3,244,586.

Controlling mealybugs means that their activity, or living members, or both, are reduced in an area. This can come about when: their populations are repulsed from an area; when they are incapacitated in or around an area; or they are exterminated, in whole, or in part, in or around an area. Of course, a combination of these results can occur. Generally, their populations, activity, or both, are desirably reduced more than fifty percent, preferably more than 90 percent.

The Synergistic Mixture can be applied to the foliar and fruiting portions of plants to control these pests. The mixture will either come in direct contact with these pests, or these pests will consume the pesticides when eating leaf, fruit mass, or extracting sap, that contains the mixture. The mixture can also be applied to the soil, and when applied in this manner, the roots can absorb the mixture taking it up into the foliar portions of the plant to control these sap feeding pests.

It should be readily apparent that the mixture may be used on, in, or around plants genetically modified to express specialized traits, such as *Bacillus thuringiensis* or other insecticidal toxins, or those expressing herbicide resistance, or those with "stacked" foreign genes expressing insecticidal toxins, herbicide resistance, nutrition-enhancement, or any other beneficial traits.

Examples

The examples are for illustration purposes and are not to be construed as limiting the invention disclosed in this document to only the embodiments disclosed in these examples.

Field Efficacy on Mealy Bug

Applications were made to cotton, *Gossypium hirsutum*, using small-plot efficacy methods. Chemicals were diluted in water and all treatments were applied using a backpack sprayer calibrated to deliver 500 liters of spray per hectare. Experimental plots measured 5 by 10 meters and each treatment was replicated three times in each trial. Prior to treatment, 20 plants that were uniformly infested with mealybug, *Pseudococcus* spp., were marked in each experimental plot. At the specified intervals after treatment, the severity of mealybug infestation on the marked plants was rated using a 0-4 scale, where 0=no infestation and 4=stunted, blackened plant. The score for each plant in each experimental plot was summed to provide a total severity score for the plot. Data were transformed to percent control relative to the untreated plots, then subjected to analysis of variance, and means were separated using Tukey's HSD (p=0.1). Expected control was calculated using the method of Colby and compared to observed control. See the Table Section for the results of the Field Trials.

Fungicides

The synergistic mixture of Sulfoxaflor and Chlorpyrifos may also be used in combination (such as, in a compositional mixture, or a simultaneous or sequential application) with one or more of the following fungicides—(3-ethoxypropyl)mercury bromide, 2-methoxyethylmercury chloride, 2-phenylphenol, 8-hydroxyquinoline sulfate, 8-phenylmercurioxyquinoline, acibenzolar, acibenzolar-5-methyl, acypetacs, acypetacs-copper, acypetacs-zinc, aldimorph, allyl alcohol, ametoctradin, amisulbrom, ampropylfos, anilazine, aureofungin, azaconazole, azithiram, azoxystrobin, barium polysulfide, benalaxyl, benalaxyl-M, benodanil, benomyl, benquinox, bentaluron, benthiavalicarb, benthiavalicarb-isopropyl, benzalkonium chloride, benzamacril, benzamacril-isobutyl, benzamorf, benzohydroxamic acid, bethoxazin, binapacryl, biphenyl, bitertanol, bithionol, bixafen, blasticidin-S, Bordeaux mixture, boscalid, bromuconazole, bupirimate, Burgundy mixture, buthiobate, butylamine, calcium polysulfide, captafol, captan, carbamorph, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, climbazole, clotrimazole, copper acetate, copper carbonate, basic, copper hydroxide, copper naphthenate, copper oleate, copper oxychloride, copper silicate, copper sulfate, copper zinc chromate, cresol, cufraneb, cuprobam, cuprous oxide, cyazofamid, cyclafuramid, cycloheximide, cyflufenamid, cymoxanil, cypendazole, cyproconazole, cyprodinil, dazomet, dazomet-sodium, DBCP, debacarb, decafentin, dehydroacetic acid, dichlofluanid, dichlone, dichlorophen, dichlozoline, diclobutrazol, diclocymet, diclomezine, diclomezine-sodium, dicloran, diethofencarb, diethyl pyrocarbonate, difenoconazole, diflumetorim, dimethirimol, dimethomorph, dimoxystrobin, diniconazole, diniconazole-M, dinobuton, dinocap, dinocap-4, dinocap-6, dinocton, dinopenton, dinosulfon, dinoterbon, diphenylamine, dipyrithione, disulfuram, ditalimfos, dithianon, DNOC, DNOC-ammonium, DNOC-potassium, DNOC-sodium, dodemorph, dodemorph acetate, dodemorph benzoate, dodicin, dodicin-sodium, dodine, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fentin, fentin chloride, fentin hydroxide, ferbam, ferimzone, fluazinam, fludioxonil, flumetover, flumorph, fluopicolide, fluopyram, fluoroimide, fluotrimazole, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, furcarbanil, furconazole, furconazole-cis, furfural, furmecyclox, furophanate, glyodin, griseofulvin, guazatine, halacrinate, hexachlorobenzene, hexachlorobutadiene, hexaconazole, hexylthiofos, hydrargaphen, hymexazol, imazalil, imazalil nitrate, imazalil sulfate, imibenconazole, iminoctadine, iminoctadine triacetate, iminoctadine trialbesilate, iodomethane, ipconazole, iprobenfos, iprodione, iprovalicarb, isoprothiolane, isopyrazam, isotianil, isovaledione, kasugamycin, kresoxim-methyl, mancopper, mancozeb, mandipropamid, maneb, mebenil, mecarbinzid, mepanipyrim, mepronil, meptyldinocap, mercuric chloride, mercuric oxide, mercurous chloride, metalaxyl, metalaxyl-M, metam, metam-ammonium, metam-potassium, metam-sodium, metazoxolon, metconazole, methasulfocarb, methfuroxam, methyl bromide, methyl isothiocyanate, methylmercury benzoate, methylmercury dicyandiamide, methylmercury pentachlorophenoxide, metiram, metominostrobin, metrafenone, metsulfovax, milneb, myclobutanil, myclozolin, N-(ethylmercury)-p-toluenesulphonanilide, nabam, natamycin, nitrostyrene, nitrothal-isopropyl, nuarimol, OCH, octhilinone, ofurace, orysastrobin, oxadixyl, oxine-copper, oxpoconazole, oxpoconazole fumarate, oxycarboxin, pefurazoate, penconazole, pencycuron, penflufen, pentachlorophenol, penthiopyrad, phenylmercuriurea, phenylmercury acetate, phenylmercury chloride, phenylmercury derivative of pyrocatechol, phenylmercury nitrate, phenylmercury salicylate, phosdiphen, phthalide, picoxystrobin, piperalin, polycarbamate, polyoxins, polyoxorim, polyoxorim-zinc, potassium azide, potassium polysulfide, potassium thiocyanate, probenazole, prochloraz, procymidone, propamocarb, propamocarb hydrochloride, propiconazole, propineb, proquinazid, prothiocarb, prothiocarb hydrochloride, prothioconazole, pyracarbolid, pyraclostrobin, pyraclostrobin, pyrametostrobin, pyraoxystrobin, pyrazophos, pyribencarb, pyridinitril, pyrifenox, pyrimethanil, pyriofenone, pyroquilon, pyroxychlor, pyroxyfur, quinacetol, quinacetol sulfate, quinazamid, quinconazole, quinoxyfen, quintozene, rabenzazole, salicylanilide, sedaxane, silthiofam, simeconazole, sodium azide, sodium orthophenylphenoxide, sodium pentachlorophenoxide, sodium polysulfide, spiroxamine, streptomycin, sulfur, sultropen, TCMTB, tebuconazole, tebufloquin, tecloftalam, tecnazene, tecoram, tetraconazole, thiabendazole, thiadifluor, thicyofen, thifluzamide, thiochlorfenphim, thiomersal, thiophanate, thiophanate-methyl, thioquinox, thiram, tiadinil, tioxymid, tolclofos-methyl, tolylfluanid, tolylmercury acetate, triadimefon, triadimenol, triamiphos, triarimol, triazbutil, triazoxide, tributyltin oxide, trichlamide, tricyclazole, tridemorph, trifloxystrobin, triflumizole, triforine, triticonazole, uniconazole, uniconazole-P, validamycin, valifenalate, vinclozolin, zarilamid, zinc naphthenate, zineb, ziram, zoxamide (collectively these commonly named fungicides are defined as the "Fungicide Group").

Herbicides

The synergistic mixture of Sulfoxaflor and Chlorpyrifos may also be used in combination (such as, in a compositional mixture, or a simultaneous or sequential application) with one or more of the following herbicides—2,3,6-TBA, 2,3,6-TBA-dimethylammonium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butomethyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 3,4-DA, 3,4-DB, 3,4-DP, 4-CPA, 4-CPB, 4-CPP, acetochlor, acifluorfen, acifluorfen-methyl, acifluorfen-sodium, aclonifen, acrolein, alachlor, allidochlor, alloxydim, alloxydim-sodium, allyl alcohol, alorac, ametridione, ametryn, amibuzin, amicarbazone, amidosulfuron, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amitrole, ammonium sulfamate, anilofos, anisuron, asulam, asulam-potassium, asulam-sodium, atraton, atrazine, azafenidin, azimsulfuron, aziprotryne, barban, BCPC, beflubutamid, benazolin, benazolin-dimethylammonium, benazolin-ethyl, benazolin-potassium, bencarbazone, benfluralin, benfuresate, bensulfuron, bensulfuron-methyl, bensulide, bentazone, bentazone-sodium, benzadox, benzadox-ammonium, benzfendizone, benzipram, benzobicyclon, benzofenap, benzofluor, benzoylprop, benzoylprop-ethyl, benzthiazuron, bicyclopyrone, bifenox, bilanafos, bilanafos-sodium, bispyribac, bispyribac-sodium, borax, bromacil, bromacil-lithium, bromacil-sodium, bromobonil, bromobutide, bromofenoxim, bromoxynil, bromoxynil butyrate, bromoxynil heptanoate, bromoxynil octanoate, bromoxynil-potassium, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, carfentrazone, carfentrazone-ethyl, CDEA, CEPC, chlomethoxyfen, chloramben, chloramben-ammonium, chloramben-diolamine, chloramben-methyl, chloramben-methylammonium, chloramben-sodium, chloranocryl, chlorazifop, chlorazifop-propargyl, chlorazine, chlorbromuron, chlorbufam, chloreturon, chlorfenac, chlorfenac-sodium, chlorfenprop, chlorfenprop-methyl, chlorflurazole, chlorflurenol, chlorflurenol-methyl, chloridazon, chlorimuron, chlorimuron-ethyl, chlomitrofen, chloropon, chlorotoluron, chloroxuron, chloroxynil, chlorprocarb, chlorpropham, chlorsulfuron, chlorthal, chlorthal-dimethyl, chlorthal-monomethyl, chlorthiamid, cinidon-ethyl, cinmethylin, cinosulfuron, cisanilide, clethodim, cliodinate, clodinafop, clodinafop-propargyl, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloransulam, cloransulam-methyl, CMA, copper sulfate, CPMF, CPPC, credazine, cresol, cumyluron, cyanamide, cyanatryn, cyanazine, cycloate, cyclosulfamuron, cycloxydim, cycluron, cyhalofop, cyhalofop-butyl, cyperquat, cyperquat chloride, cyprazine, cyprazole, cypromid, daimuron, dalapon, dalapon-calcium, dalapon-magnesium, dalapon-sodium, dazomet, dazomet-sodium, delachlor, desmedipham, desmetryn, di-allate, dicamba, dicamba-dimethylammonium, dicamba-diolamine, dicamba-isopropylammonium, dicamba-methyl, dicamba-olamine, dicamba-potassium, dicamba-sodium, dicamba-trolamine, dichlobenil, dichloralurea, dichlormate, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-dimethylammonium, dichlorprop-potassium, dichlorprop-sodium, diclofop, diclofop-methyl, diclosulam, diethamquat, diethamquat dichloride, diethatyl, diethatyl-ethyl, difenopenten, difenopenten-ethyl, difenoxuron, difenzoquat, difenzoquat metilsulfate, diflufenican, diflufenzopyr, diflufenzopyr-sodium, dimefuron, dimepiperate, dimethachlor, dimethametryn, dimethenamid, dimethenamid-P, dimexano, dimidazon, dinitramine, dinofenate, dinoprop, dinosam, dinoseb, dinoseb acetate, dinoseb-ammonium, dinoseb-diolamine, dinoseb-sodium, dinoseb-trolamine, dinoterb, dinoterb acetate, diphacinone-sodium, diphenamid, dipropetryn, diquat, diquat dibromide, disul, disul-sodium, dithiopyr, diuron, DMPA, DNOC, DNOC-ammonium, DNOC-potassium, DNOC-sodium, DSMA, EBEP, eglinazine, eglinazine-ethyl, endothal, endothal-diammonium, endothal-dipotassium, endothal-disodium, epronaz, EPTC, erbon, esprocarb, ethalfluralin, ethametsulfuron, ethametsulfuron-methyl, ethidimuron, ethiolate, ethofumesate, ethoxyfen, ethoxyfen-ethyl, ethoxysulfuron, etinofen, etnipromid, etobenzanid, EXD, fenasulam, fenoprop, fenoprop-3-butoxypropyl, fenoprop-butomethyl, fenoprop-butotyl, fenoprop-butyl, fenoprop-isoctyl, fenoprop-methyl, fenoprop-potassium, fenoxaprop, fenoxaprop-ethyl, fenoxaprop-P, fenoxaprop-P-ethyl, fenoxasulfone, fenteracol, fenthiaprop, fenthiaprop-ethyl, fentrazamide, fenuron, fenuron TCA, ferrous sulfate, flamprop, flamprop-isopropyl, flamprop-M, flamprop-methyl, flamprop-M-isopropyl, flamprop-M-methyl, flazasulfuron, florasulam, fluazifop, fluazifop-butyl, fluazifop-methyl, fluazifop-P, fluazifop-P-butyl, fluazolate, flucarbazone, flucarbazone-sodium, flucetosulfuron, fluchloralin, flufenacet, flufenican, flufenpyr, flufenpyr-ethyl, flumetsulam, flumezin, flumiclorac, flumiclorac-pentyl, flumioxazin, flumipropyn, fluometuron, fluorodifen, fluoroglycofen, fluoroglycofen-ethyl, fluoromidine, fluoronitrofen, fluothiuron, flupoxam, flupropacil, flupropanate, flupropanate-sodium, flupyrsulfuron, flupyrsulfuron-methyl-sodium, fluridone, fluorochloridone, fluoroxypyr, fluoroxypyr-butomethyl, fluoroxypyr-meptyl, flurtamone, fluthiacet, fluthiacet-methyl, fomesafen, fomesafen-sodium, foramsulfuron, fosamine, fosamine-ammonium, furyloxyfen, glufosinate, glufosinate-ammonium, glufosinate-P, glufosinate-P-ammonium, glufosinate-P-sodium, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, hexachloroacetone, hexaflurate, hexazinone, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, indanofan, indaziflam, iodobonil, iodomethane, iodosulfuron, iodosulfuron-methyl-sodium, ioxynil, ioxynil octanoate, ioxynil-lithium, ioxynil-sodium, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-dimethylammonium, mecoprop-P-isobutyl, mecoprop-potassium, mecoprop-P-potassium, mecoprop-sodium, mecoprop-trolamine, medinoterb, medinoterb acetate, mefenacet, mefluidide, mefluidide-diolamine, mefluidide-potassium, mesoprazine, mesosulfuron, mesosulfuron-methyl, mesotrione, metam, metam-ammonium, metamifop, metamitron, metam-potassium, metam-sodium, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metolachlor, metosulam, metoxuron, metribuzin, metsulfuron, metsulfuron-methyl, molinate, monalide, monisouron, monochloroacetic acid, monolinuron, monuron, monuron TCA, morfamquat, morfamquat dichloride, MSMA, naproanilide, napropamide, naptalam, naptalam-sodium, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxapyrazon-dimolamine, oxapyrazon-sodium, oxasulfuron, oxaziclomefone, oxyfluorfen, parafluoron, paraquat, paraquat dichloride, paraquat dimetilsulfate, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picloram-2-ethylhexyl, picloram-isoctyl, picloram-methyl, picloramolamine, picloram-potassium, picloram-triethylammonium, picloram-tris(2-hydroxypropyl)ammonium, picolinafen, pinoxaden, piperophos, potassium arsenite, potassium azide, potassium cyanate, pretilachlor, primisulfuron, primisulfuron-methyl, procyazine, prodiamine, profluazol, profluralin, profoxydim, proglinazine, proglinazine-ethyl, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, proxan, proxan-sodium, prynachlor, pydanon, pyraclonil, pyraflufen, pyraflufen-ethyl, pyrasulfotole, pyrazolynate, pyrazosulfuron, pyrazosulfuron-ethyl, pyrazoxyfen, pyribenzoxim, pyributicarb, pyriclor, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quinonamid, quizalofop, quizalofop-ethyl, quizalofop-P, quizalofop-P-ethyl, quizalofop-P-tefuryl, rhodethanil, rimsulfuron, saflufenacil, sebuthylazine, secbumeton, sethoxydim, siduron, simazine, simeton, simetryn, SMA, S-metolachlor, sodium arsenite, sodium azide, sodium chlorate, sulcotrione, sulfallate, sulfentrazone, sulfometuron, sulfometuron-methyl, sulfosulfuron, sulfuric acid, sulglycapin, swep, TCA, TCA-ammonium, TCA-calcium, TCA-ethadyl, TCA-magnesium, TCA-sodium, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone, thiencarbazone-methyl, thifensulfuron, thifensulfuron-methyl, thiobencarb, tiocarbazil, tioclorim, topramezone, tralkoxydim, tri-allate, triasulfuron, triaziflam, tribenuron, tribenuron-methyl, tricamba, triclopyr, triclopyr-butotyl, triclopyr-ethyl, triclopyr-triethylammonium, tridiphane, trietazine, trifloxysulfuron, trifloxysulfuron-sodium, trifluralin, triflusulfuron, triflusulfuron-methyl, trifop, trifop-methyl, trifopsime, trihydroxytriazine, trimeturon, tripropindan, tritac, tritosulfuron, vernolate, xylachlor, (collectively these commonly named herbicides are defined as the "Herbicide Group").

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions. For further information on formulation types see "Catalogue of Pesticide Formulation Types and International Coding System" Technical Monograph n°2, 5th Edition by CropLife International (2002).

Pesticides are applied most often as aqueous suspensions or emulsions prepared from concentrated formulations of such pesticides. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually chosen from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They can be used in pest harborages.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use, this embodiment will be referred to as "OIWE".

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mallis, 9th Edition, copyright 2004 by GIE Media Inc.

Other Formulation Components

These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspoemulsions, and ultra low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

For further information, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

The headings in this document are for convenience only and must not be used to interpret any portion hereof.

TABLE SECTION

TABLE 1

Synergism of Sulfoxaflor and Chlorpyrifos on Mealy Bug - Results from Trial A.

| Treatment | Rate (g/ha) | % Control | | |
|---|---|---|---|---|
| | | 3 DAT | 7 DAT | 11 DAT |
| Sulfoxaflor | 50 | 17.56 b | 21.65 c | 20.68 c |
| Chlorpyrifos | 500 | 35.64 c | 43.34 b | 43.60 b |
| Sulfoxaflor + Chlorpyrifos | 50 + 500 | 51.27 a | 61.94 a | 58.60 a |
| Untreated | | 0 d | 0 d | 0 d |

DAT—Days after treatment

Means followed by the same letter are not significantly different (Tukey's HSD, P = 0.1).

The results of Trial A clearly indicate that the synergistic mixture of Sulfoxaflor and Chlorpyrifos was statistically significantly superior to Sulfoxaflor or Chlorpyrifos alone.

TABLE 2

Synergism of Sulfoxaflor and Chlorpyrifos on Mealy Bug - Results from Trial B.

| Treatment | Rate (g/ha) | % Control | | | |
|---|---|---|---|---|---|
| | | 3 DAT | 7 DAT | 11 DAT | 14 DAT |
| Sulfoxaflor | 50 | −2.66 b | 7.81 b | 7.81 b | 5.32 b |
| Chlorpyrifos | 500 | 35.23 a | 38.80 a | 33.51 a | 26.89 a |
| Sulfoxaflor + Chlorpyrifos | 50 + 500 | 46.81 a | 53.02 a | 52.18 a | 38.25 a |
| Untreated | | 0.0 b | 0.0 b | 0.0 b | 0.0 b |

DAT—Days after treatment

Means followed by the same letter are not significantly different (Tukey's HSD, P = 0.1).

The results of Trial B clearly indicate that the synergistic mixture of Sulfoxaflor and Chlorpyrifos was statistically significantly superior to Sulfoxaflor alone and better than Chlorpyrifos alone.

TABLE 3

Synergism of Sulfoxaflor and Chlorpyrifos on Mealy Bug - Results from Trial C.

| Treatment | Rate (g/ha) | % Control | | | |
|---|---|---|---|---|---|
| | | 4 DAT | 8 DAT | 11 DAT | 14 DAT |
| Sulfoxaflor | 50 | 7.39 c | 9.19 b | 4.76 b | 2.49 bc |
| Chlorpyrifos | 500 | 36.44 b | 33.37 a | 28.24 a | 23.03 ab |
| Sulfoxaflor + Chlorpyrifos | 50 + 500 | 56.39 a | 47.52 a | 44.27 a | 30.14 a |
| Untreated | | 0.0 c | 0.0 b | 0.0 b | 0.0 c |

DAT—Days after treatment

Means followed by the same letter are not significantly different (Tukey's HSD, P = 0.1).

The results of Trial C clearly indicate that the synergistic mixture of Sulfoxaflor and Chlorpyrifos was statistically significantly superior to Sulfoxaflor alone and better than Chlorpyrifos alone.

TABLE 4

Summary of Colby analysis for synergism (difference between observed and expected control) in Trials A, B and C. A positive "Difference" value indicates synergism.

| Trial | DAT | % Control Sulfoxaflor Alone | % Control Chlorpyrifos Alone | % Control Sulfoxaflor and Chlorpyrifos: Observed | % Control Sulfoxaflor and Chlorpyrifos: Expected | Difference |
|---|---|---|---|---|---|---|
| A | 3 | 17.56 | 35.64 | 51.27 | 46.9 | 4.3 |
|   | 7 | 21.65 | 43.34 | 61.94 | 55.6 | 6.3 |
|   | 11 | 20.68 | 43.60 | 58.60 | 55.3 | 3.3 |
| B | 3 | −2.66 | 35.23 | 46.81 | 33.5 | 13.3 |
|   | 7 | 7.81 | 38.80 | 53.02 | 43.6 | 9.4 |
|   | 11 | 7.81 | 33.51 | 52.18 | 38.7 | 13.5 |
|   | 14 | 5.32 | 26.89 | 38.25 | 30.8 | 7.5 |
| C | 4 | 7.39 | 36.44 | 56.39 | 41.1 | 15.3 |
|   | 8 | 9.19 | 33.37 | 47.52 | 39.5 | 8.0 |
|   | 11 | 4.76 | 28.24 | 44.27 | 31.7 | 12.6 |
|   | 14 | 2.49 | 23.03 | 30.14 | 24.9 | 5.2 |

DAT—Days after treatment
This summary clearly shows that in all Trials synergism was discovered.

We claim:

1. A process to control mealybugs said process comprising applying, to a locus where cotton is growing, wherein said locus is inhabited with mealybugs, a synergistic composition consisting essentially of Chlorpyrifos (or Chlorpyrifos-methyl) and Sulfoxaflor, wherein said synergistic composition the weight ratio of Chlorpyrifos (or Chlorpyrifos-methyl) to Sulfoxaflor is from about 10:1 to about 5:1.

* * * * *